United States Patent [19]

Crane

[11] Patent Number: 4,661,369
[45] Date of Patent: Apr. 28, 1987

[54] NON-DESTRUCTIVE EVALUATION METHOD FOR COATED CARBON-CARBON COMPOSITES

[75] Inventor: Robert L. Crane, Kettering, Ohio

[73] Assignee: The United States of America as represented by the Secretary of the Air Force, Washington, D.C.

[21] Appl. No.: 772,815

[22] Filed: Sep. 5, 1985

[51] Int. Cl.$^4$ .............................................. B32B 35/00
[52] U.S. Cl. ........................................ 427/8; 427/140; 427/376.2; 427/379; 427/397.7
[58] Field of Search ................ 427/140, 8, 376.2, 427, 427/430.1, DIG. 11, DIG. 10, 372.2, 397.7, 379; 73/104

[56] References Cited

U.S. PATENT DOCUMENTS

| | | | |
|---|---|---|---|
| 2,516,857 | 8/1950 | de Forest et al. | 73/104 |
| 2,597,964 | 5/1952 | Winter | 427/DIG. 11 |
| 2,635,329 | 4/1953 | de Forest et al. | 29/148 |
| 2,636,127 | 4/1953 | de Forest et al. | 250/71 |
| 2,676,487 | 4/1954 | Clarke | 73/104 |
| 2,707,236 | 4/1955 | de Forest | 250/71 |
| 2,795,951 | 6/1957 | Butler | 73/104 |
| 3,811,928 | 5/1974 | Henney et al. | 427/DIG. 10 |
| 3,845,658 | 11/1974 | Conway | 73/104 |
| 3,930,407 | 1/1976 | Alburger | 73/104 |
| 4,090,402 | 5/1978 | Alburger | 73/104 |
| 4,161,505 | 7/1979 | Shiraishi et al. | 427/376.2 |
| 4,273,671 | 6/1981 | Allinikov | 73/104 |

FOREIGN PATENT DOCUMENTS

| | | | |
|---|---|---|---|
| 59-155039 | 9/1984 | Japan | 427/376.2 |
| 546371 | 7/1942 | United Kingdom | 427/376.2 |
| 760623 | 11/1956 | United Kingdom | 427/376.2 |

*Primary Examiner*—Sadie L. Childs
*Attorney, Agent, or Firm*—Charles E. Bricker; Donald J. Singer

[57] ABSTRACT

A non-destructive technique for detecting and repairing surface flaws in the silicon carbide oxidation resistant coating of a carbon-carbon composite. The surface of the composite is treated with a test liquid consisting essentially of a carrier fluid, a particulate pigment and a finely divided borosilicate glass, or a mixture of silicon dioxide and boron oxide, containing 0.25 to 8 weight percent boron oxide. The treated surface is inspected for surface flaws. Any discovered flaws are repaired by heating the surface to cause the borosilicate glass to flow and heal the flaw. The composite is thereafter heated to a further elevated temperature to deplete the boron from the flaw-sealing glass.

4 Claims, No Drawings

NON-DESTRUCTIVE EVALUATION METHOD FOR COATED CARBON-CARBON COMPOSITES

RIGHTS OF THE GOVERNMENT

The invention described herein may be manufactured and used by or for the Government of the United States for all governmental purposes without the payment of any royalty.

BACKGROUND OF THE INVENTION

This invention relates to a method for detecting and healing flaws in the oxidation protective surface coating of a carbon-carbon composite material.

Reinforced composites are used in a wide variety of applications. The best known composites are made from two-dimensional fabrics and/or fibers dispersed in a resin or plastic matrix. These composites are basically a resin or plastic structure to which reinforcing fabrics or fibers have been added to enhance the physical properties of the structure.

Advances in the field of aerospace technology have created a need for high strength, temperature-resistant materials. For many applications, this need is satisfied by carbon-carbon composite materials. These materials utilize a carbon matrix, as opposed to a resin or plastic matrix.

A wide range of multidirectional reinforced composite structures are now available. The simplest of these structures is obtained by stacking unidirectional fibers or sheets with alternating layers oriented in different directions, or by stacking woven sheets. More complex structures provide three-dimensional reinforcement. The simplest of the three-dimensional structures is the three-directional (3D) structure which generally has reinforcing elements which are mutually orthogonal. The most complex three-dimensional structure is a thirteen-directional (13D) structure. The thirteen directions, with reference to a cube, form three subgroups; the three edges, the four long diagonals, and the six diagonals of the faces.

The reinforced carbon-carbon composite structures are fabricated from graphite or carbon yarn or rods. The term yarn includes continuous filament yarns and yarns spun from short fibers, and comprises a plurality of filaments or fibers combined to make up a desired end count. Rods are produced by a pultrusion process whereby unidirectional groups of carbon or graphite yarn are assembled and impregnated with a thermosetting or thermoplastic resin or binder. The impregnated yarn groups are drawn through a die which is warmed to a desired temperature and which has a suitable shape.

The carbon or graphite yarns or rods are assembled into the desired geometric structure. If desired, the yarn may be impregnated with a suitable resin or binder prior to assembly.

The composite is formed either by sintering the reinforcement structure by solidifying the impregnated precursor, thereby avoiding the requirement for other materials, or by the dry or the liquid process, or by a combination of these methods. The dry process consists of depositing pyrolytic carbon inside the structure of the reinforcement by decomposition of a hydrocarbon gas such as methane. In the liquid process, the porous texture of the reinforcement is impregnated with a thermosetting resin or a thermoplastic carbon precursor, such as a phenolic resin, a furanyl resin, coal tar pitch, or the like, that is converted to carbon by heat treatment. Following carbonization, the structure is graphitized. The impregnation, carbonization, graphitization cycle is repeated as often as necessary to densify the composite to a desired degree.

The process of densification of the composite generally comprises heat treatment at a temperature in the range of 2500° to 3000° C. and may include isostatic pressing at pressures up to about 15,000 psi in an oxygen-free environment.

Many applications for carbon-carbon composites have been proposed or implemented. The use of such composites for re-entry heat shield applications has been demonstrated. Ehrenreich, U.S. Pat. No. 3,672,936, discloses disk brake pads made of such composites. The use of these materials for turbine disk and blade components, for propulsion system nozzles, thrust chambers, and ramjet combustion liners, and for re-entry vehicle nosetip applications has been investigated.

In the presence of an inert atmosphere, carbon has a sublimation point in excess of 3500° C. When heated in excess oxygen, carbon burns at about 400° C. For certain applications an allowable amount of wasting away due to combustion can be designed into the structure. For example, a re-entry vehicle heat shield is intended for a useful life of one cycle. For other applications, use and multiple re-use may be desired, in which case wasting away is to be avoided.

Oxidation resistance can be be provided for carbon or graphite materials by depositing silicon over the carbon. Rubisch, U.S. Pat. No. 3,553,010, discloses that flame injection applied silicon reacts with the carbon of the underlying body forming silicon carbide when the operational temperature of the protected parts exceeds about 550° C., which leads to a protective layer of silicon carbide which exhibits oxidation resistance at a relatively high temperature. When heated in the presence of oxygen, the silicon carbide is converted to silicon dioxide which has a very high viscosity when compared to any other glass.

The protective layer of silicon carbide is highly flaw sensitive. If this protective layer is breached, the underlying carbon structure can be quickly oxidized due to the inability of the silica layer to flow and seal the ends of the damaged protective layer. Breach of the silicon carbide layer may occur during densification following application of the silicon carbide layer, as when pressure and/or temperature changes are inadvertently done too rapidly.

The detection and characterization of oxidation initiating defects is particularly difficult in coated C/C materials because the porous nature of both the coating and substrate renders conventional techniques such as fluorescent penetrants or ultrasonics virtually useless. Each pore and crack produces a defect signal and the recognition of the significant defects in this background ranges from exceedingly difficult to impossible. Since the through-the-thickness cracks may be the most important defects that lead to catastrophic oxidation of the substrate and since they occur naturally due to the mismatch in thermal expansions of the substrate and the coating, the healing of these flaws could increase substantially the reliability of coated C/C components.

Accordingly, it is an object of the present invention to provide a method for detecting and healing cracks in the SiC protective coating of a C-C composite.

Other objects and advantages of this invention will be readily apparent from the following description of certain preferred embodiments thereof.

SUMMARY OF THE INVENTION

In accordance with the present invention there is provided a method for detecting and repairing surface flaws in the oxidation resistant coating of a carbon-carbon composite which comprises the steps of:

(a) providing a test liquid composition consisting essentially of a carrier fluid, at least one particulate pigment material which is insoluble in the carrier fluid, finely divided silicon dioxide, and about 0.25 to 8 weight percent boron oxide, based upon the weight of silicon dioxide;

(b) applying the test liquid to the surface of the composite;

(c) inspecting the surface for surface flaws;

(d) heating the composite at least in the area of discovered surface flaws to fuse the boron oxide and silicon oxide to form a coherent, flaw-sealing oxidation protection coating in the surface flaws; and, (e) further heating the composite to deplete boron from the flaw-sealing coating.

DESCRIPTION OF THE PREFERRED EMBODIMENT

The test liquid composition comprises a carrier fluid, at least one particulate pigment material which is insoluble in the carrier fluid, finely divided silicon dioxide and about 0.25 to 8 weight percent of boron oxide, based on the weight of silicon dioxide. Alternatively, the test liquid composition can comprise a borosilicate glass which contains about 0.25 to 8 weight percent of boron oxide, in place of the mixture of silicon dioxide and boron oxide.

The carrier fluid can be any fluid which is normally liquid at about room temperature, which can be evaporated at a temperature of up to about 100° C., which leaves no residue upon evaporation and which is not reactive with a carbon-carbon composite structure. Several liquids satisfy these criteria, including water and low molecular weight alcohols, ethers, ketones, and the like. The low molecular weight alcohols are presently preferred because of availability, ease of removal, no residue upon evaporation and wetability. Suitable alcohols include methyl, ethyl, propyl, isopropyl and the like.

The particulate pigment material can be any material which is brightly colored and/or will fluoresce when excited by ultraviolet light. Particularly suitable are micro-encapsulated dyes, such as Day-Glo Blaze Orange and Day-Glo Saturn Yellow, available from the Day-Glo Color Corp., Cleveland, OH. The particulate pigment material is employed in an amount of about 0.01 to about 1.0 volume percent, based on the carrier fluid.

The quantity of silicon dioxide or borosilicate glass in the test liquid composition can range from about 0.1 to about 5.0 volume percent, based on the carrier fluid.

The solid materials, i.e., pigment, silicon dioxide and boron oxide should have a particulate size in the nominal range of about 1 to 150 microns.

The solid materials are mixed into the carrier fluid, then the resulting test fluid is applied to the composite surface to be tested. Application can be accomplished by flooding the surface or by spraying the test liquid onto the surface or by dipping the composite item into the test liquid. Flaws in the oxidation resistant coating are paths for rapid absorption of the carrier fluid. During absorption of the carrier fluid, the solid particles are deposited in or near the flaw by settling out of the fluid or by being filtered out due to the relatively smaller flaw size compared to the size of the particles.

It is within the scope of the invention to prewet the surface of the composite to be tested with water, water containing a small amount (e.g., about 1% w/w) of surfactant, or another suitable liquid. Prewetting the surface in this manner tends to limit the absorption of the carrier fluid in defect-free areas, while not substantially altering absorption at through-the-thickness flaws.

Following application of the test liquid, the fluid carrier is allowed to evaporate. If desired, evaporation can be hastened using an elevated temperature, reduced pressure, enhanced air flow, or a combination of any of these.

The dried composite surface is then inspected for flaws using normal light and/or ultraviolet light. If flaws are discovered, the flawed surface can be heated to an elevated temperature, but below about 400° C., to fuse the borosilicate glass particles into low-melting, relatively low viscosity glass, which easily flows into and costs and seals any flaws. The temperature can then be increased to the intended operating temperature. Inasmuch as the flaws are sealed, contact of the carbon substrate with oxygen is prevented. Boron oxide has a relatively high vapor pressure; accordingly, the flaw-sealing glass is quickly depleted of boron, leaving a viscous, nearly pure quartz glass in the flaws to further inhibit oxygen transport to the substrate.

Various modifications may be made in the present invention without departing from the spirit thereof or the scope of the following claims.

I claim:

1. A method for detecting and repairing surface flaws in the silicon carbide oxidation resistant coating of a carbon-carbon composite which comprises the steps of:
    (a) providing a test liquid composition consisting essentially of a carrier fluid, at least one particulate pigment which is insoluble in said carrier fluid, finely divided silicon dioxide, and about 0.25 to 8 weight percent boron oxide, based upon the weight of the silicon dioxide;
    (b) applying said test liquid to the surface of said composite;
    (c) inspecting said surface for surface flaws;
    (d) heating said composite in at least the area of discovered surface flaws to an elevated temperature to fuse said boron oxide and said silicon oxide to form a coherent flaw-sealing coating in said surface flaws; and
    (e) thereafter heating said composite to a further elevated temperature to deplete boron from said flaw-sealing coating.

2. The method of claim 1 wherein said test fluid composition consists essentially of about 0.1 to 5.0 volume percent of silicon dioxide, about 0.01 to 1.0 volume percent of pigment material and about 0.25 to 8 weight percent of boron oxide.

3. The method of claim 2 wherein said carrier fluid is a low molecular weight alcohol.

4. The method of claim 2 wherein said pigment material is a micro-encapsulated dye.

* * * * *